US00RE44762E

(19) United States
(12) Reissued Patent
Hyon et al.

(10) Patent Number: US RE44,762 E
(45) Date of Reissued Patent: Feb. 11, 2014

(54) ULTRA HIGH MOLECULAR WEIGHT POLYETHYLENE MOLDED ARTICLE FOR ARTIFICIAL JOINTS AND METHOD OF PREPARING THE SAME

(75) Inventors: Suong-Hyu Hyon, Kyoto (JP); Masanori Oka, Nara (JP); Hiroki Takahashi, legal representative, Kyoto (JP)

(73) Assignee: BMG Incorporated, Kyoto (JP)

(21) Appl. No.: 13/531,232

(22) Filed: Jun. 22, 2012

Related U.S. Patent Documents

Reissue of:
(64) Patent No.: 6,168,626
Issued: Jan. 2, 2001
Appl. No.: 08/640,738
PCT Filed: Sep. 18, 1995
PCT No.: PCT/JP95/01858
§ 371 (c)(1),
(2), (4) Date: May 6, 1996
PCT Pub. No.: WO96/09330
PCT Pub. Date: Mar. 28, 1996

U.S. Applications:
(60) Continuation of application No. 10/643,674, filed on Aug. 19, 2003, now abandoned, which is a division of application No. 10/141,374, filed on May 8, 2002.

(30) Foreign Application Priority Data

Sep. 21, 1994 (JP) ..... 6-254564

(51) Int. Cl.
*C08J 3/28* (2006.01)
*C08G 61/04* (2006.01)

(52) U.S. Cl.
USPC ..... 522/153; 522/150; 522/1; 522/161; 522/157; 520/1

(58) Field of Classification Search
USPC ..... 522/153, 150, 1, 161, 157; 520/1
See application file for complete search history.

(56) References Cited

U.S. PATENT DOCUMENTS

| | | | |
|---|---|---|---|
| 2,948,666 | A | 8/1960 | Lawton |
| 3,362,897 | A | 1/1968 | Lawton |
| 3,563,870 | A | 2/1971 | Tung et al. |
| 3,886,056 | A | 5/1975 | Kitamaru et al. |
| 3,956,253 | A | 5/1976 | Braun |
| 4,055,862 | A | 11/1977 | Farling |
| 4,171,338 | A | 10/1979 | Mason |
| 4,224,696 | A | 9/1980 | Murray et al. |
| 4,265,959 | A | 5/1981 | Sano et al. |
| 4,281,420 | A | 8/1981 | Raab |
| 4,348,350 | A | 9/1982 | Meier et al. |
| 4,390,666 | A | 6/1983 | Moriguchi et al. |
| 4,582,656 | A | 4/1986 | Hoffmann |
| 4,586,995 | A | 5/1986 | Randall et al. |
| 4,587,163 | A | 5/1986 | Zachariades |
| 4,636,340 | A | 1/1987 | Itaba et al. |
| 4,655,769 | A | 4/1987 | Zachariades |
| 4,668,577 | A | 5/1987 | Ohta et al. |
| 4,747,990 | A | 5/1988 | Gaussens et al. |
| 4,778,633 | A | 10/1988 | Kiang et al. |
| 4,902,460 | A | 2/1990 | Yagi et al. |
| 5,030,402 | A | 7/1991 | Zachariades |
| 5,030,487 | A | 7/1991 | Rosenzweig |
| 5,037,928 | A | 8/1991 | Li et al. |
| 5,066,755 | A | 11/1991 | Lemstra |
| 5,130,376 | A | 7/1992 | Shih |
| 5,160,464 | A | 11/1992 | Ward et al. |
| 5,200,439 | A | 4/1993 | Asanuma |
| 5,204,045 | A | 4/1993 | Courval et al. |
| 5,210,130 | A | 5/1993 | Howard, Jr. |
| 5,234,652 | A | 8/1993 | Woodhams et al. |
| 5,276,079 | A | 1/1994 | Duan et al. |
| 5,358,529 | A | 10/1994 | Davidson |
| 5,405,393 | A | 4/1995 | Falkenström |
| 5,414,049 | A | 5/1995 | Sun et al. |
| 5,428,079 | A | 6/1995 | Bastiaansen et al. |
| 5,439,949 | A | 8/1995 | Lucas et al. |
| 5,449,745 | A | 9/1995 | Sun et al. |
| 5,466,530 | A | 11/1995 | England et al. |
| 5,478,906 | A | 12/1995 | Howard, Jr. |
| 5,505,900 | A | 4/1996 | Suwanda et al. |
| 5,508,319 | A | 4/1996 | DeNicola, Jr. et al. |

(Continued)

FOREIGN PATENT DOCUMENTS

| | | |
|---|---|---|
| CA | 1 257 745 | 7/1989 |
| JP | 57-211347 | 12/1982 |

(Continued)

OTHER PUBLICATIONS

"Researchers Get Awards for Orthopaedic Research", The American Academy of Orthopaedic Surgeons, News Release. (Mar. 19, 1998), available at http://www.aaos.org/wordhtml/press/98press/kappa.htm. (4 pages).

(Continued)

*Primary Examiner* — Ling Choi
*Assistant Examiner* — Jessica E Whiteley
(74) *Attorney, Agent, or Firm* — Harness, Dickey

(57) ABSTRACT

An ultra high molecular weight polyethylene molded article for artificial joints has molecular orientation or crystal orientation in the molded article, and is low in friction and is superior in abrasion resistance, and therefore is available as components for artificial joints. Further, the ultra high molecular weight polyethylene molded article for artificial joints can be used as a component for artificial hip joints (artificial acetabular cup), a component for artificial knee joints (artificial tibial insert) and the socket for artificial elbow joints, and in addition to the medical use, it can be applied as materials for various industries by utilizing the characteristics such as low friction and superior abrasion resistance.

23 Claims, No Drawings

(56) References Cited

U.S. PATENT DOCUMENTS

| | | | |
|---|---|---|---|
| 5,543,471 | A | 8/1996 | Sun et al. |
| 5,552,104 | A | 9/1996 | DeNicola, Jr. et al. |
| 5,577,368 | A | 11/1996 | Hamilton et al. |
| 5,650,485 | A | 7/1997 | Sun et al. |
| 5,684,124 | A | 11/1997 | Howard, Jr. et al. |
| 5,709,020 | A | 1/1998 | Pienkowski et al. |
| 5,728,748 | A | 3/1998 | Sun et al. |
| 5,824,411 | A | 10/1998 | Shalaby et al. |
| 5,879,400 | A | 3/1999 | Merrill et al. |
| 6,017,975 | A | 1/2000 | Saum et al. |
| 6,048,480 | A | 4/2000 | Doyle |
| 6,146,426 | A | 11/2000 | Doyle |
| 6,165,220 | A | 12/2000 | McKellop et al. |
| 6,174,934 | B1 | 1/2001 | Sun et al. |
| 6,184,265 | B1 | 2/2001 | Hamilton et al. |
| 6,228,900 | B1 | 5/2001 | Shen et al. |
| 6,281,264 | B1 | 8/2001 | Salovey et al. |
| 6,355,215 | B1 | 3/2002 | Poggie et al. |
| 6,365,089 | B1 | 4/2002 | Krebs et al. |
| 6,372,814 | B1 | 4/2002 | Sun et al. |
| 6,458,727 | B1 | 10/2002 | Jones et al. |
| 6,494,917 | B1 | 12/2002 | McKellop et al. |
| 6,664,308 | B2 | 12/2003 | Sun et al. |
| 6,818,020 | B2 | 11/2004 | Sun et al. |
| 2001/0049401 | A1 | 12/2001 | Salovey et al. |
| 2002/0037944 | A1 | 3/2002 | Shen et al. |
| 2002/0107300 | A1 | 8/2002 | Saum et al. |
| 2002/0125614 | A1 | 9/2002 | King et al. |
| 2002/0161438 | A1 | 10/2002 | Scott et al. |
| 2003/0045603 | A1 | 3/2003 | Salovey et al. |
| 2003/0119935 | A1 | 6/2003 | Merrill et al. |
| 2003/0130743 | A1 | 7/2003 | Scott et al. |
| 2003/0149125 | A1 | 8/2003 | Muratoglu et al. |
| 2003/0158287 | A1 | 8/2003 | Salovey et al. |
| 2004/0208841 | A1 | 10/2004 | Salovey et al. |
| 2005/0059750 | A1 | 3/2005 | Sun et al. |

FOREIGN PATENT DOCUMENTS

| | | |
|---|---|---|
| JP | 62-243634 | 10/1987 |
| JP | 02-175137 | 7/1990 |
| JP | 04-198201 | 7/1992 |
| JP | 05-507748 | 11/1993 |
| JP | 91 022222 | 5/1997 |
| WO | WO 93/10953 | 6/1993 |
| WO | WO 95/06148 | 3/1995 |
| WO | WO 98/01085 | 1/1998 |

OTHER PUBLICATIONS

"Researchers to Get Kappa Delta Awards for Achievements" The American Academy of Orthopaedic Surgeons, Academy News. (Mar. 19, 1998), available at http://www.aaos.org/wordhtml/98news/kappa.htm. (3 pages).

Appleby et al. "Post-Gamma Irradiation Cross-linking of Polyethylene Tape by Acetylene Treatment" Journal of Materials Science. vol. 29 (1994) p. 227-231.

Appleby et al. "Property Modification of Polyethylene Tapes by Acetylene-Sensitized Gamma Irradiation" Journal of Materials Science. vol. 29 (1994) p. 151-156.

Bhateja et al. "Radiation-Induced Crystallinity Changes in Polyethylene Blends" Journal of Materials Science. vol. 20 (1985) p. 2839-2845.

Bhateja, S. "Radiation-Induced Crystallinity Changes in Linear Polyethylene" Journal of Polymer Science: Polymer Physics Edition. vol. 21 (1983) p. 523-536.

Bhateja, S. "Radiation-Induced Crystallinity Changes in Linear Polyethylene: Influence of Aging" Journal of Applied Polymer Science. vol. 28 (1983) p. 861-872.

Bhateja, S. "Radiation-Induced Crystallinity Changes in Pressure-Crystallized Ultrahigh Molecular Weight Polyethylene" J. Macromol. Sci. Phys. B22(1) (1983) p. 159-168.

Bowman, J. "The Processing and Properties of y-Irradiated HDPE Granules" Intern. Polymer Processing III. (1988) p. 211-220.

Chen et al. "Radiation-Induced Crosslinking: II. Effect on the Crystalline and Amorphous Densities of Polyethylene" Colloid Polym Sci. vol. 269 (1991) p. 469-476.

Chen et al. "Radiation-Induced Crosslinking: III. Effect on the Crystalline and Amorphous Density Fluctuations of Polyethylene" Colloid Polym Sci. vol. 269 (1991) p. 353-363.

Choudhury et al. "The Effects of Irradiation and Ageing on the Abrasive Wear Resistance of Ultra High Molecular Weight Polyethylene" Wear Elsevier Science. vol. 203-204 (1997) p. 335-340.

Chu et al. "Some Structures and Properties of Very High Molecular Weight Linear Polyethylene" Bull. Inst. Chem. Res. vol. 47, No. 3 (1969) p. 209-221.

Collier et al. "Polyethylene: The Past, Present and Future" The American Academy of Orthopaedic Surgeons, 1999 Annual Meeting Scientific Program, available at http://www.aaos.org/wordhtml/anmeet99/sciprog/g.htm. (20 pages).

Crugnola et al., Ultrahigh Molecular Weight Polyethylene as Used in Articular Prostheses (A Molecular Weight Distribution Study), J. of App. Polymer Science, vol. 20, (1976) pp. 809-812.

Dijkstra et al. "Cross-linking of Ultra-high Molecular Weight Polyethylene in the Melt by Means of Electron Beam Irradiation" Polymer. vol. 30 (May 1989) p. 866-873.

Dole et al. "Crystallinity and Crosslinking Efficiency in the Irradiation of Polyethylene" Radiat. Phys. Chem. vol. 14 (1979) p. 711-720.

du Plessis et al. "The Improvement of Polyethylene Prostheses Through Radiation Crosslinking" Radiat. Phys. Chem. vol. 9 (1977) p. 647-652.

Edit by Polymer Society "Polymer Functional Material Series (vol. 9) Medical Treatment Functional Material", Nov. 20, 1990, Kyoritsu Shuppan K.K., p. 165-166.

Edit by Polymer Society "Polymer New Material One Point (vol. 20) Medical Polymer Material", Feb. 20, 1989, Kyoritsu Shuppan K.K., p. 45-46.

Ellis et al., The Use of Ultrahigh Molecular Weight Polyethylene in Articular Prostheses—II. Effects of Fabrication and Gamma Sterilization on Polymer Characteristics, Coatings and Plastics Preprints, vol. 37, No. 2, American Chemical Society, (1977) pp. 280-284.

Ellwanger et al. "Very High Pressure Molding of Ultra High Molecular Weight Polyethylene (UHMWPE)" ANTEC. (1987) p. 572-574.

Gauvin et al., "Investigation of the Radio Frequency Heating Process for UHMWPE" ANTEC. (1987) p. 575-578.

Handlos, V. "Enhanced Crosslinking of Polyethylene" Radiat. Phys. Chem. vol. 14 (1979) p. 721-728.

Howmedica, Material Properties, Product Quality Control, and Their Relation to UHMWPE Performance, Part Two of a Series on Ultra-High Molecular Weight Polyethylene, (1994) pp. 1-20.

Howmedica, Overview and Fundamentals of UHMWPE, Part One of a Series on Ultra-High Molecular Weight Polyethylene, (1994) pp. 1-8.

Jahan et al. "Combined Chemical and Mechanical Effects on Free Radicals in UHMWPE Joints During Implantation" Journal of Biomedical Materials Research. vol. 25 (1991) p. 1005-1017.

Jones et al., Effect of γ Irradiation on the Friction and Wear of Ultrahigh Molecular weight Polyethylene, Wear, vol. 70, (1981) pp. 77-92.

Kang et al. "The Radiation Chemistry of Polyethylene IX. Temperaure Coefficient of Cross-Linking and Other Effects" Journal of the American Chemical Society. vol. 89:9 (1967) p. 1980-1986.

Kanig, G. "Further Electron Microscope Observations on Polyethylene III. Smectic Intermediate State During Melting and Crystallization" Colloid Polym Sci. vol. 269 (1991) p. 1118-1125.

Kashiwabara et al., Radiation-Induced Oxidation of Plastics, Radiation Processing of Polymers, Chapter 11, (1992) pp. 221-254.

Kato et al. "Structural Changes and Melting Behavior of γ-Irradiated Polyethylene" Japanese Journal of Applied Physics. vol. 20, No. 4. (Apr. 1981) p. 691-697.

Kitamaru et al. "Size and Orientation of Cristallites in Lightly Cross-linked Polyethylene, Crystallized from the Melt Under Uniaxial Compression" Die Makromolekulare Chemie. vol. 175 (1974) p. 255-275.

(56) References Cited

OTHER PUBLICATIONS

Kitamaru et al. "Structure and Properties of Lightly Crosslinked Crystalline Polymers Crystallized or Processed Under Molecular Orientation" Journal of Polymer Science: Macromolecular Reviews. vol. 14 (1979) p. 207-264.
Kitamaru et al. "The Properties of Transparent Film Made from Linear Polyethylene by Irradiation Cross-Linking" Properties of Transparent Film. vol. 6, No. 3 (May-Jun. 1973) p. 337-343.
Kitamaru et al. "A Commentary Remark on the Isothermal Crystallization of a Polyethylene Gel from the Stretched Molten State" Bull. Inst. Chem. Res. vol. 46, No. 2 (1968) p. 97-106.
Kurth et al., "Effects of Radiation Sterilization on UHMW-Polyethylene" ANTEC. (1987) p. 1193-1197.
Lin et al. "Review Structure and Plastic Deformation of Polyethylene" Journal of Materials Science. vol. 29 (1994) p. 294-323.
Matsubara et al. "The Wear Properties of High-Density Polyethylene Irradiated by Gamma Rays" Wear. vol. 10 (1967) p. 214-222.
Meyer, B. "Recent Developments in Radiation Sterilizable Plastics" ANTEC. (1987) p. 1190-1192.
Minkova et al. "Blends of Normal High Density and Ultra-High Molecular Weight Polyethylene, γ Irradiated at a Low Dose" Colloid Polym Sci. vol. 268 (1990) p. 1018-1023.
Minkova, L. "DSC of γ-Irradiated Ultra-High Molecular Weight Polyethylene and High Density Polyethylene of Normal Molecular Weight" Colloid Polym Sci. vol. 266 (1988) p. 6-10.
Muratoglu et al. "A Novel Method of Cross-Linking Ultra-High-Molecular Weight Polyethylene to Improve Wear, Reduce Oxidation, and Retain Mechanical Properties" The Journal of Arthroplasty. vol. 16, No. 2 (2001) p. 149-160.
Nakayama et al. "Structure and Mechanical Properties of Ultra-High Molecular Weight Polyethylene Deformed Near Melting Temperature" Pure & Appl. Chem. vol. 63, No. 12 (1991) p. 1793-1804.
Narkis et al., Structure and Tensile Behavior of Irradiation—and Peroxide—Crosslinked Polyethylenes, J. Macromol. Sci. - Phys., vol. B 26, No. 1, (1987) pp. 37-58.
Nusbaum et al., The Effects of Radiation Sterilization on the Properties of Ultrahigh Molecular Weight Polyethylene, Journal of Biomedical Materials Research, vol. 13, (1979) pp. 557-576.
O'Neill et al. "The Distribution of Oxidation Products in Irradiated Ultra-High Molecular Weight Polyethylene" Polymer Degradation and Stability. vol. 49 (1995) p. 239-244.
Oonishi et al. "Comparison of Wear of UHMWPE Sliding Against Metal and Alumina in Total Hip Prostheses—Wear Test and Clinical Results" 3rd World Biomaterials Congress, Transactions. (Apr. 1988) p. 337.
Oonishi et al. "Comparisons of Wear of UHMW Polyethylene Sliding Against Metal and Alumina in Total Hip Prostheses" Bioceramics. vol. 1 (1989) p. 272-277.
Oonishi et al. "Effect of Cross-Linkage by Gamma Radiation in Heavy Doses to Low Wear Polyethylene in Total Hip Prostheses" Journal of Materials Science: Materials in Medicine. vol. 7 (1996) p. 753-763.
Oonishi et al. "Improvement of Polyethylene by Irradiation in Artificial Joints" Radiat. Phys. Chem. vol. 39, No. 6 (1992) p. 495-504.
Oonishi et al. "In Vivo and In Vitro Wear Behaviour on Weightbearing Surfaces of Polyethylene Sockets Improved by Irradiation in Total Hip Prostheses" Surface Modification Technologies V. (1992) p. 101-112.
Oonishi et al. "SEM Observation on the Clinically Used Gamma-Irradiated Reinforced HDP Socket in Total Hip Replacement" Clinical Implant Materials, Advances in Biomaterials. vol. 9 (1990) p. 379-384.
Oonishi et al. "The Optimum Dose of Gamma Radiation-Heavy Doses to Low Wear Polyethylene in Total Hip Prostheses" Journal of Materials Science Materials in Medicine. vol. 8 (1997) p. 11-18.
Oonishi et al. "Wear Resistance of Gamma-Ray Irradiated U.H.M.W. Polyethylene Socket in Total Hip Prosthesis—Wear Test and Long Term Clinical Results" MRS Int'l. Mtg. On Adv. Mats. vol. 1 (1989) p. 351-356.
Oonishi et al. "Wear Resistance of Gamma-Ray Irradiated UHMWPE Socket in Total Hip Prostheses—Wear Test and Long Term Clinical Results" 3rd World Biomaterials Congress, Transactions. (Apr. 1988) p. 588.
Patel, G. "Acceleration of Radiation-Induced Crosslinking in Polyethylene by Diacetylenes" Radiat. Phys. Chem. vol. 14 (1979) p. 729-735.
Premnath et al. "Gamma Sterilization of UHMWPE Articular Implants: an Analysis of the Oxidation Problem" Biomaterials. vol. 17 (1996) p. 1741-1753.
Rimnac et al. "Chemical and Mechanical Degradation of UHMWPE: Report of the Development of an In Vitro Test" Journal of Applied Biomaterials. vol. 5 (1994) p. 17-21.
Rose et al. "Exploratory Investigations on the Structure Dependence of the Wear Resistance of Polyethylene" Wear. vol. 77 (1982) p. 89-104.
Salovey et al. "Irradiation of Ultra High Molecular Weight Polyethylene" Polymer Preprints. vol. 26, No. 1 (1985) p. 118-119.
Salovey, R. "On the Morphology of Crosslinking Polymers" Polymer Letters. vol. 2 (1964) p. 833-834.
Sandford et al. "Shelf Life Prediction of Radiation Sterilized Medical Devices" ANTEC (1987) p. 1201-1204.
Sawatari et al. "Crosslinking Effect of Ultrahigh Molecular Weight Polyethylene-Low Molecular Weight Polyethylene Blend Films Produced by Gelation/Crystallization From Solutions" Colloid Polym Sci. vol. 269, No. 8 (1991) p. 795-806.
Shen et al. "The Friction and Wear Behavior of Irradiated Very High Molecular Weight Polyethylene" Wear. vol. 30 (1974) p. 349-364.
Shinde et al. "Irradiation of Ultrahigh-Molecular-Weight Polyethylene" Journal of Polymer Science: Polymer Physics Edition. vol. 23 (Feb. 1985) p. 1681-1689.
Silverman, Radiation-Induced and Chemical Crosslinking: A Brief Comparison, Radiation Processing of Polymers, Chap. 2, (1992) p. 15-22.
Streicher, R. "Change in Properties of High Molecular Weight Polyethylenes After Ionizing Irradiation for Sterilization and Modification" Third International Conference on Radiation Processing for Plastics and Rubber (Nov. 1987) (9 pages).
Streicher, R. "Influence of Ionizing Irradiation in Air and Nitrogen for Sterilization of Surgical Grade Polyethylene for Implants" Radiat. Phys. Chem. vol. 31, Nos. 4-6 (1988) p. 693-698.
Streicher, R. "Investigation on Sterilization and Modification of High Molecular Weight Polyethylenes by Ionizing Irradiation" Reprint from beta-gamma 1/89 p. 34-43.
Streicher, R. "Ionizing Irradiation for Sterilization and Modification of High Molecular Weight Polyethylenes" Plastics and Rubber Processing and Applications. vol. 10, (1988) p. 221-229.
Streicher, R. "UHMW—Polyethylen als Werkstoff für artikulierende Komponenten von Gelenkendoprothesen (UHMW Polyethylene Used as a Material for the Articulating Components of Endoprostheses)" Biomed. Technik, vol. 38 (1993) p. 303-313.
Sultan et al., Advances in Crosslinking Technology, Plastics, Rubber and Composites Processing and Applications 21, (1994) pp. 65-73.
Sun et al. "Development of an Accelerated Aging Method for Evaluation of Long-term Irradiation Effects on UHMWPE Implants" Howmedica Inc., Pfizer Hospital Products Group. (1996) p. 969-970.
Waldman et al. "Compressive Stress Relaxation Behavior of Irradiated Ultra-High Molecular Weight Polyethylene at 37° C." Journal of Applied Biomaterials. vol. 5 (1994) p. 333-338.
Wang et al. "Melting of Ultrahigh Molecular Weight Polyethylene" Journal of Applied Polymer Science. vol. 34 (1987) p. 593-599.
Ward, I. "New Developments in the Production of High Modulus and High Strength Flexible Polymers" Progr Colloid Polym Sci. vol. 92 (1993) p. 103-110.
Williams, J. "Radiation Stability of Polypropylene" ANTEC. (1987) p. 1198-1200.
Wilson et al. "Proton Modification of Ultra High Molecular Weight Polyethylene to Promote Crosslinking for Enhanced Chemical and Physical Properties" Mat. Res. Soc. Symp. Proc. vol. 396 (1996) p. 311-316.
Wong et al. "Molecular Deformation Processes in Gel-Spun Polyethylene Fibres" Journal of Materials Science. vol. 29 (1994) p. 520-526.

(56) References Cited

OTHER PUBLICATIONS

Yongxiang et al., Crosslinking of Wire and Cable Insulation Using Electron Accelerators, Radiation Processing of Polymers, Chap. 5, (1992) pp. 71-92.

Zhao et al. "Effect of Irradiation on Crystallinity and Mechanical Properties of Ultrahigh Molecular Weight Polyethylene" Journal of Applied Polymer Science. vol. 50 (1993) p. 1797-1801.

Zoepfl et al. "Differential Scanning Calorimetry Studies of Irradiated Polyethylene: I. Melting Temperatures and Fusion Endotherms" Journal of Polymer Science: Polymer Chemistry Edition. vol. 22 (1984) p. 2017-2032.

Zoepfl et al. "Differential Scanning Calorimetry Studies of Irradated Polyethylene: II. The Effect of Oxygen" Journal of Polymer Science: Polymer Chemistry Edition. vol. 22 (1984) p. 2033-2045.

ULTRA HIGH MOLECULAR WEIGHT POLYETHYLENE MOLDED ARTICLE FOR ARTIFICIAL JOINTS AND METHOD OF PREPARING THE SAME

Matter enclosed in heavy brackets [ ] appears in the original patent but forms no part of this reissue specification; matter printed in italics indicates the additions made by reissue.

*More than one reissue application has been filed for the reissue of U.S. Pat. No. 6,168,626. The reissue applications are: Ser. No. 10/141,374 filed May 8, 2002; Ser. No. 10/643,674 filed Aug. 19, 2003, a divisional reissue of Ser. No. 10/141,374; and Ser. No. 11/522,504 filed Sep. 15, 2006, a continuation reissue of (now abandoned) Ser. No. 10/643,673 (which was a divisional reissue of Ser. No. 10/141,374); and the current application, a continuation reissue of Ser. No. 10/643,674.*

TECHNICAL FIELD

The present invention relates to an ultra high molecular weight polyethylene molded article suitable for artificial joints having molecular orientation or crystal orientation and to a method of preparing the same.

BACKGROUND ART

Thirty years or more have passed since an artificial joint was developed and applied clinically to patients suffering from any diseases of arthritis. Since then, benefits given by the artificial joint have been great in the sense of social welfare because, for example, patients with chronic rheumatism have been able to walk again and to return to public life. On the other hand, however, serious problems have occurred, particularly late appearing complications caused by total joint arthroplasty, a high rate of "loosening" in the implant components, and the necessity of revision of the joint with a surgical operation due to osteolysis around the implanted artificial joint.

These artificial joints includes an artificial hip joint, an artificial knee joint, an artificial elbow joint, an artificial finger joint, artificial shoulder joint and the like. Among those joints, it is necessary for the artificial hip joint and artificial knee joint to have high mechanical strength because gravity corresponding to several times the patient's body weight is applied to them. Therefore, materials for the artificial joint at present are constituted of a hard material of metal or ceramic and a soft socket of an ultra high molecular weight polyethylene (UHMWPE). While the UHMWPE constituting such a socket is superior in abrasion resistance as compared with polymeric materials such as polytetrafluoroethylene and polycarbonate, the UHMWPE is inferior in properties such as low abrasion resistance and stress relaxation to impact load which are inherently possessed by articular cartilage of living body. Also, reaction caused by a foreign matter has been a serious problem wherein macrophages proliferate against wear debris of the UHMWPE socket, i.e. component and an abnormal granulation tissue generated thereby causes resorption of the bone.

After artificial joints were developed, though some improvements in qualities of material and design have been made, for example, a cementless artificial joint and the like with respect to the hard material, there has been no remarkable progress for about thirty years with respect to the soft socket portion except that the UHMWPE was employed. And if the artificial joint is used for a long period of time, numerous wear debris of polyethylene are produced because of friction between the hard material such as metal and the UHMWPE of the socket. By considering the osteolysis due to granulation tissue containing a foreign matter which is caused by the wear debris, further improvement of abrasion resistance is indispensable. As an attempt to reduce the abrasion of UHMWPE, it can be considered to select a material for the hard material and to improve the UHMWPE. Though the irradiation of an ultra high dose of γ-ray was tried for improving the UHMWPE, it was made clear that coefficient of abrasion increases and abrasion loss does not decrease. Also, though the improvement to increase molecular weight of the UHMWPE was made and a weight-average molecular weight of the UHMWPE at present has been increased to approximately 5 to 8 million, it is difficult to make a UHMWPE having a far ultra high molecular weight. Further, considerable improvement in dynamic properties can scarcely be expected even if a UHMWPE having a weight-average molecular weight of 10 million could be synthesized. Thus, it is regarded that any improvement in dynamic properties of the UHMWPE by chemical modification reached its limitation, and it is regarded to be difficult to obtain a UHMWPE molded article having a more excellent abrasion resistance and lower friction.

It is well-known that Carothers of E.I. Du Pont developed, first all over the world, a synthetic fiber, i.e., Nylon, and greatly contributed industrially. As means for improving mechanical properties of this synthetic fiber, uniaxial stretching in the direction of fiber axis is carried out industrially. Also, to improve the strength of the film, biaxial stretching and rolling are carried out industrially. In accordance with these methods, mechanical properties can be increased considerably by giving uniaxial orientation or biaxial orientation to molecules or crystals.

From these points of view, there is an idea that orientation is given to molecules or crystals in the polymer structure to improve the mechanical properties. However, any technologies cannot endow molecules or crystals with orientation in a large molded article in the form of block, and it is not easy to consider enablement of a method.

Then, the present inventors tried to obtain a molded article of a low friction and to improve an abrasion resistance by introducing molecular orientation or crystal orientation into a finished product by means of, not a chemical modification method, but a physical modification method.

This approach has never been attempted, not only in Japan, but also in other countries. The idea to endow the polyethylene molded article for artificial joints with molecular orientation or crystal orientation is the very creative, and it is sure that this invention, if actually carried out, will be applied to artificial joints all over the world. Also, this invention will be revolutionary in terms of industrial innovation whereby disadvantages which have been problems for the past thirty years are improved.

DISCLOSURE OF THE INVENTION

The invention relates to an ultra high molecular weight polyethylene (UHMWPE) molded article for artificial joints and to an artificial join comprising the UHMWPE molded article.

This UHMWPE molded article having molecular orientation or crystal orientation can be obtained by irradiating a low dose of a high energy ray to a raw UHMWPE molded article to introduce a very small amount of crosslinking points in polymer chains so as to be crosslinked slightly, then by compression-deforming the crosslinked UHMWPE molded article after heating up to its compression-deformable temperature, and by cooling the molded article while keeping the deformed state.

The UHMWPE molded article having molecular orientation or crystal orientation (hereinafter referred to as "oriented UHMWPE molded article") of the present invention has a low friction and remarkably improved abrasion resistance. And, the artificial joint comprising the oriented UHMWPE molded article has a smooth lubricity and reduced amount of abrasion loss.

BEST MODE FOR CARRYING OUT INVENTION

The oriented UHMWPE molded article of the invention has molecular orientation or crystal orientation within the molded article. The meaning of "to have molecular orientation within the molded article" is that polymer chains are oriented perpendicular to the direction of the compression, namely, oriented to the direction of the flow of the molecular chains. The meaning of "to have crystal orientation" is that the crystal planes in polyethylene such as (200) plane and (110) plane are oriented to the direction parallel to the compression plane, namely, that the crystal planes are oriented. Also, the presence of these orientations can be known by means of biefringence measurements, infrared spectra and X-ray diffraction. And, a coefficient of friction of the molded article decreases and abrasion loss also decreases by endowing with those orientations. Also, other functional properties, for example, tensile strength and tensile modulus are improved, and also density, thermal properties (melting point, heat of fusion) and the like are improved.

As described above, the oriented UHMWPE molded article can be obtained by irradiating a high energy ray to raw UHMWPE and then heating up and compression-deforming the UHMWPE, followed by cooling and solidifying.

As the raw UHMWPE, one having a weight-average molecular weight of 2 to 8 million, preferably 5 to 7 million is used. The melting point thereof is approximately 136° to 139° C. The raw UHMWPE is used usually in the form of block, and may be used in the form of rod.

Every kind of high energy rays can be employed as the high energy ray to be irradiated, for example a radioactive ray such as γ-ray or X-ray, an electron beam, a neutron ray and the like. Among them, γ-ray is superior in views of availability of irradiation apparatus and excellent permeability to materials. This irradiation of the high energy ray is carried out to generate crosslinking points in the molecular chains of the UHMWPE and then to produce intermolecular crosslinkage. The density of crosslinking is preferably such a very small degree that the crystallization is not prevented with ensuring a large elastic-deformation, for example 0.1 to 10, particularly 1 to 2 crosslinking points per one molecular chain.

With respect to the irradiation atmosphere, if oxygen exists, it is not preferable since a decomposition (cleavage) occurs simultaneously, and therefore the atmosphere of a vacuum or of an inert gas such as $N_2$ or argon is preferable. The temperature of the atmosphere may be room temperature and also may be a higher temperature of not less than the crystal transition point (80° C.).

The dose of irradiation (energy) is very important. If the dose of irradiation is too high, the density of crosslinking becomes higher, and the bridged structure is destroyed if a large deformation is applied in the subsequent process. And, even if the molten state is made, such a degree of elastic deformation required to obtain the desired molecular orientation or crystal orientation cannot be given. As a result, it is obliged to decrease a degree of the deformation, and it becomes impossible to obtain the molecular orientation or crystal orientation which is necessary for molecular chains in the molded article. On the other hand, in case that a dose of irradiation is too low or not irradiation is carried out, molecular chains are fluidized in the manner of viscous fluidity without stretching to be plastic-deformed, resulting in that the molecular orientation or crystal orientation cannot be obtained. A preferable dose of irradiation (energy) is the dose to give the above-mentioned density of crosslinking and 0.01 to 5.0 MR, preferably 0.1 to 3 MR in case of radioactive rays.

The UHMWPE molded article which is crosslinked slightly by irradiating with the high energy ray has an infinite weight-average molecular weight because it is crosslinked, and the melting point thereof changes not so much and is 136° and 139° C.

Then, this slightly crosslinked UHMWPE molded article is heated up to a compression-deformable temperature. The compression-deformable temperature of is a temperature of around or not less than the melting point of the crosslinked UHMWPE, and is concretely from the melting point minus 50° C. to the melting point plus 80° C. It is most suitable to heat up to a temperature of not less than the melting point, particularly preferably 160° to 220° C., further preferably 180° to 200° C. to melt completely. The compression-deformation can be carried out, however, at a temperature of even around the melting point, for example 100° to 130° C. If completely melted, since the crosslinked UHMWPE is in the state of rubber to possess rubber elasticity, the compression-deformation is easily carried out.

The compression-deformation is carried out under a pressure of 30 to 200 kgf/cm$^2$, usually 50 to 100 kgf/cm$^2$, with heating at the above-mentioned temperature in a die suitable for the use or be using a hot press machine. It is sufficient that a degree of the compression is approximately ⅓ to 1/10 of an original thickness in case of a molded article in the form of block. The deformation of the crosslinked UHMWPE molded article of the present invention is a rubber elastic deformation because molecular chains are crosslinked slightly, and after the molecular chains are stretched to give the necessary molecular orientation, then cooled as they are and crystallized, the crystal orientation can be obtained. On the other hand, non-crosslinked, namely non-irradiated UHMWPE molded article is fluid-deformed when heated and compressed at a temperature of not less than the melting point, and thus molecular orientation or crystal orientation cannot be obtained.

Then, the UHMWPE molded article having the molecular orientation or crystal orientation obtained by the compression-deformation as described above is cooled and solidified while keeping the deformed state. If the deformed state is set free before solidification, the stretched molecular chains are relaxed in stress to return to the original state because the compression-deformation is conducted in the molten state. That is, the molecular orientation or crystal orientation in the UHMWPE molded article is relaxed in a moment. Therefore, the deformed state must not be set free until solidified.

As the cooling method, there are rapid coolings such as water-cooling and air-cooling as well as standing to cool, and the cooling is carried out down to room temperature, preferably to a temperature of around 20° to 40° C. Further, it is preferable to cool at a constant rate under a condition of 10° C./min, preferably 1° C./min to obtain excellent dynamic properties because the cooling rate has a great influence on the crystallinity, particularly on the degree of crystallinity of the produced molded article. The completion of the solidification can be confirmed by decrease of a pressure guage (the volume being shrinked after the completion of the crystallization).

Also, before the cooling, the compression-deformed UHMWPE molded article may be subjected to isothermal crystallization at around 100° to 130° C., preferably 110° to 120° C., for 1 to 20 hours, preferably 5 to 10 hours, with keeping the deformed state, and then cooled to room temperature, preferably to 40° C. and solidified. When carrying out the isothermal crystallization, the degree of crystallinity becomes higher and the dynamic properties are improved. The cooling after the isothermal crystallization is not particularly limited and cooling at a rate of 1° C./min is preferable.

The melting point of the UHMWPE molded article having the molecular orientation or crystal orientation obtained by the cooling and solidification is 135° to 155° C.

The compression-deformed molded article which is obtained as described above can also be processed to a socket for artificial joints by cutting and can be molded by means of the compression-deformation mold with a die comprising a convex and concave portions. The surface hardness can be further reinforced by introducing metal ions, e.g. titanium, zirconium, iron, molybdenum, aluminium and/or cobalt ion, into the UHMWPE molded article for artificial joints which is obtained by cutting the compression-deformed molded article.

Hereinafter, the present invention is explained concretely by referring to Preparation Examples and Examples.

PREPARATION EXAMPLES 1 TO 3

A block of UHMWPE (thickness 3 cm, width 5 cm, length 5 cm) having a weight-average molecular weight of approximately 6 million and a melting point of 138° C. was put in a glass ampul and the glass was sealed after reducing the inner pressure ($10^{-2}$ to $10^{-3}$ mmHg) under vacuum. γ-Ray from cobalt 60 was irradiated at a dose of 0.5 MR to this glass ampul at 25° C. Then, the UHMWPE block irradiated by the radioactive ray (melting point: 138° C., weight-average molecular weight: infinite) was taken out from the glass ampul, melted completely at 200° C. by using at hot press, compressed to ⅓, $\frac{1}{4.5}$ and ⅙ of the original thickness by applying a pressure of 50 kgf/cm$^2$m and then cooled to room temperature through natural cooling with keeping the deformed state.

COMPARATIVE PREPARATION EXAMPLES 1 TO 3

The same raw UHMWPE block as was used in Preparation Examples 1 to 3 was compressed to ⅓, $\frac{1}{4.5}$ and ⅙ of the original thickness after melting completely at 200° C. by using a hot press in the same way without irradiation, and cooled naturally to room temperature with keeping the deformed state.

PREPARATION EXAMPLES 4 TO 6

Irradiated UHMWPE molded articles were obtained by compression-deforming and cooling naturally similarly in Preparation Example 1 except that a dose of irradiation of γ-ray was changed to 1.0 MR, 1.5 MR or 2.0 MR. Each weight-average molecular weights of the 1.0 MR irradiated article, 1.5 MR irradiated article and 2.0 MR irradiated article were infinite, and the melting points thereof were almost constant and were 138° C.

PREPARATION EXAMPLE 7

An irradiated UHMWPE molded article was obtained similarly in Preparation Example 1 except that after the irradiation of γ-ray (0.5 MR), the temperature was raised to 130° C. and the compression-deformation to ⅓ was carried out under a pressure of 200 kgf/cm$^3$ for 5 minutes.

PREPARATION EXAMPLE 8

An irradiated UHMWPE molded article was obtained similarly in Preparation Example 1 except that after the compression molding, isothermal crystallization was carried out for 10 hours at 120° C. and then natural cooling was carried out.

EXAMPLE 1

A test sample having a thickness of 7 mm and a diameter of 7 mm was prepared by cutting from the UHMWPE molded article obtained in each of Preparation Examples 1 to 8 and Comparative Preparation Examples 1 to 3, and wear factor and coefficient of friction were evaluated by measuring a friction force and wear factor as the following.

Testing apparatus and testing conditions:

The unidirectional Pin-On-Disc wear and friction testing machine manufactured by Research Center for Biomedical Engineering, Kyoto University, was used for the test.

The unidirectional-type testing machine is operated by pressing a test sample on a surface of a ceramic disc, which is rotating in the clockwise direction, by means of the arm-type loading method. The load can be varied by providing a weight to the one end of the arm. The rotation of the disc is transmitted to a bearing by way of a belt according to the rotation of an invertor-controlled motor. The testing speed was set to 50 mm/s. Also, all tests were carried out in 50 ml saline for 48 hours and the temperature of the liquid was kept at 25±2° C.

Means to measure frictional force and wear volume:

A friction force was measured by a lever type dynamometer fixed to the arm portion of the testing machine. The friction force was recorded with a pen recorder with the lapse of time. The friction coefficients shown in test results (Table 1) were determined in case of a sliding distance of 8640 m (48 hours after tests begin).

The wear volume was evaluated by compressing the rotating disc of zirconia at a pressure of 1 MPa and by measuring the decreased thickness of the test sample with a non-contact type capacitance level gauge.

The test for each test sample was carried out three times under each loading condition, and the coefficient of friction and coefficient of abrasion were calculated in average value. In this case, the surface of the zirconia disc was made in intentionally roughened to Ra; 0.2 to 0.3, and the wear volume was measured after 48 hours.

Wear factor and coefficient of friction were calculated according to the equation of Dowson et al.

Wear Factor (WF)=Wear volume (mm$^3$)/{Load (N)×Sliding distance (m)}

Coefficient of friction (CF)=Friction force (N)/Load (N)

The test results are shown in Table 1. With respect to the non-irradiated sample, there is no substantial difference in the wear factor (WF), that is, WF of $15.3\times10^{-7}$ for the sample having the compression ratio at deformation (original thickness/thickness after compression-deformation) of 3, WF of $16.4\times10^{-7}$ for the compression ratio of 4.5, and WF of $14.9\times10^{-7}$ for the compression ratio of 6.

Remarkable decrease was observed, however, with respect to the 0.5 MR irradiated sample, i.e. WF if $9.07\times10^{-7}$ for the compression ratio of 3, WF of $2.78\times10^{-7}$ for the compression ratio of 4.5, and WF of $5.31\times10^{-8}$ for the compression ratio of 6.

EXAMPLE 2

Characteristics of the UHMWPE molded articles obtained in Preparation Example 3 and Comparative Preparation Example 3 are shown in Table 2.

The heat of fusion and melting point were measured at a scan speed of 10° C./min by means of DSC-50 of SHIMADZU CORPORATION. And, the tensile strength and Young's modulus were measured at a tensile rate of 100%/min by means of Autograph S-100 of SHIMADZU CORPORATION.

As shown in Table 2, the density and melting point of UHMWPE molded article obtained from the 0.5 MR irraidation test of Preparation Example 3 are higher and the tensile strength and Young's modulus thereof increase, as compared with those of the UHMWPE molded article obtained from the non-irradiation test of Comparative Preparation Example 3. Particularly, the melting point rises from 138.0° to 149.5° C.

TABLE 1

| | Dose of irradiation MR | Compression deformation Temperature (° C.) | Compression ratio | Cooling | Wear factor (WF) | Coefficient of friction (CF) |
|---|---|---|---|---|---|---|
| Preparation Example | | | | | | |
| 1 | 0.5 | 200 | 3 | standing to cool | $9.07\times10^{-7}$ | 0.11 |
| 2 | 0.5 | 200 | 4.5 | standing to cool | $2.78\times10^{-7}$ | 0.08 |
| 3 | 0.5 | 200 | 6 | standing to cool | $5.31\times10^{-8}$ | 0.03 |
| 4 | 1.0 | 200 | 3 | standing to cool | $7.35\times10^{-7}$ | 0.04 |
| 5 | 1.5 | 200 | 3 | standing to cool | $4.62\times10^{-7}$ | 0.02 |
| 6 | 2.0 | 200 | 3 | standing to cool | $8.31\times10^{-8}$ | 0.01 |
| 7 | 1.0 | 130 | 3 | standing to cool | $9.64\times10^{-7}$ | 0.12 |
| 8 | 1.0 | 200 | 3 | allowed to cool after the isothermal crystallization for 10 hours at 120° C. | $2.53\times10^{-8}$ | 0.01 |
| Comparative Preparation Example | | | | | | |
| 1 | — | 200 | 3 | standing to cool | $15.3\times10^{-7}$ | 0.14 |
| 2 | — | 200 | 4.5 | standing to cool | $16.4\times10^{-7}$ | 0.15 |
| 3 | — | 200 | 6 | standing to cool | $14.9\times10^{-7}$ | 0.12 |

TABLE 2

| Sample | Density (g/cm$^3$) | Heat of fusion (cal/g) | Melting point (° C.) | Tensile strength (kg/cm$^2$) | Young's modulus (kg/cm$^2$) |
|---|---|---|---|---|---|
| Comparative Preparation Example 3 | 0.931 | 31.6 | 138.0 | $0.3\times10^3$ | $1.36\times10^4$ |
| Preparation Example 3 | 0.948 | 39.2 | 149.5 | $1.3\times10^3$ | $1.95\times10^4$ |

INDUSTRIAL APPLICABILITY

The ultra high molecular weight polyethylene molded article for artificial joints obtained according to the present invention has the molecular orientation or crystal orientation in the molded article, and is low in friction and is superior in abrasion resistance, and therefore is available as a components of artificial joints.

Further, the ultra high molecular weight polyethylene molded article for artificial joints of the present invention can be used as a component for artificial hip joints (artificial acetabular cup), a component for artificial knee joints (artificial tibial insert) and the socket for artificial elbow joints, and in addition to the medical use, it can be applied as materials for various industries by utilizing the characteristics such as low friction and superior abrasion resistance.

What is claimed is:

[1. An ultra high molecular weight polyethylene molded block having a molecular weight not less than 5 million, having been crosslinked slightly and having been compression-deformed in a direction perpendicular to a compression plane, cooled and solidified in a compression-deformed state under pressure so as to have orientation of crystal planes in a direction parallel to the compression plane, and a thickness range of 5 to 10 mm in a direction perpendicular to the compression plane.]

[2. The molded block of claim 1, wherein a melting temperature of the ultra high molecular weight polyethylene is in a range of 135 to 155° C.]

[3. A method for producing an ultra high molecular weight polyethylene molded block having orientation of crystal planes in a direction parallel to a compression plane, comprising slightly crosslinking an ultra high molecular weight polyethylene molded block having a molecular weight not less than 5 million by irradiating the block with a high energy ray and thereby introducing a very small amount of crosslinking points into molecular chains of the block, then heating the crosslinked ultra high molecular weight polyethylene molded block up to a compression deformable temperature, compression-deforming the block by compressing the block in a direction perpendicular to the compression plane so as to deform the block, and then cooling the block while keeping the block in a deformed state under pressure, said block after cooling having a thickness range of 5 to 10 mm in a direction perpendicular to the compression plane.]

[4. The method of claim 3, where the high energy ray is a radioactive ray and a dose of the irradiation is in the range of 0.01 to 5.0 MR.]

[5. The method of claim 3 or 4, wherein the compression-deformable temperature is in a range of 50° C. lower than a melting temperature of the crosslinked ultra high molecular weight polyethylene to 80° C. higher than the melting temperature.]

[6. The method of claim 3, 4 or 5 wherein a weight-average molecular weight of the ultra high molecular weight polyethylene before irradiation is in a range of 2 to 8 million.]

[7. An ultra molecular weight polyethylene molded block having orientation of crystal planes in a direction parallel to a compression plane, said block produced by slightly crosslinking an ultra high molecular weight polyethylene block having a molecular weight of not less than 5 million by irradiating the block with a high energy ray and thereby introducing a very small amount of crosslinking points into molecular chains of the block, then heating the crosslinked block up to a compression deformable temperature, compression-deforming the block by compressing the block in a direction perpendicular to the compression plane so as to deform the block, and then cooling and solidifying the block while keeping the block in a deformed state under pressure, said block after cooling and solidifying having a thickness range of 5 to 10 mm in a direction perpendicular to the compression plane.]

[8. Artificial joint for implantation in a joint of an animal, the joint comprising a joint component formed from an ultra high molecular weight polyethylene molded block having a molecular weight of not less than 5 million, having been crosslinked slightly and having been compression-deformed in a direction perpendicular to a compression plane, cooled and solidified in a compression-deformed state under pressure so as to have orientation of crystal planes in a direction parallel to the compression plane, said block having a thickness range of 5 to 10 mm in a direction perpendicular to the compression plane.]

[9. Artificial joint according to claim 8, the joint for implantation in a joint of a human being.]

[10. Artificial joint for implantation in a joint of an animal, the joint comprising a joint component formed from an ultra high molecular weight polyethylene molded block having a molecular weight of not less than 5 million, having been crosslinked slightly and having been compression-deformed in a direction perpendicular to a compression plane so as to have orientation of crystal planes in a direction parallel to the compression plane, wherein said block having a thickness range of 5 to 10 mm in a direction perpendicular to the compression plane and the melting temperature of the molded block is in a range of 135 to 155° C.]

[11. Artificial joint according to claim 10, the joint for implantation in a joint of a human being.]

*12. A method for producing an ultra high molecular weight polyethylene (UHMWPE) artificial hip component, UHMWPE artificial knee component, UHMWPE artificial elbow component, UHMWPE artificial finger component, or UHMWPE artificial shoulder component having improved abrasion resistance, comprising:*

*(a) crosslinking an ultra high molecular weight polyethylene block having a molecular weight not less than 5 million by irradiating the block with a high energy radiation at a level of at least 1 MR;*

*(b) heating said crosslinked block up to a compression deformable temperature below the melting point of the UHMWPE;*

*(c) subjecting said heated block to pressure; then*

*(d) cooling said block; and*

*(e) processing said cooled block to form said component.*

*13. A method for producing an ultra high molecular weight polyethylene artificial joint component according to claim 12, wherein said irradiation is gamma irradiation at a level of from 1 MR to 5 MR.*

*14. A method for producing an ultra high molecular weight polyethylene artificial joint component according to claim 12, wherein said heating is in a range of from 50° C. lower than the melting temperature of the crosslinked ultra high molecular weight polyethylene to the melting temperature.*

*15. A method for producing an ultra high molecular weight polyethylene artificial joint component according to claim 12, wherein said pressure is applied so as to deform the block.*

*16. A method for producing an ultra high molecular weight polyethylene artificial joint component according to claim 15, wherein said deformation is in a direction perpendicular to the plane of compression.*

*17. A method for producing an ultra high molecular weight polyethylene artificial joint component according to claim 16, wherein said block is cooled in a compression-deformed state under pressure.*

*18. A method for producing an ultra high molecular weight polyethylene artificial joint component according to claim 17, wherein said block has an orientation of crystal planes in a direction parallel to the compression plane.*

*19. A method for producing an ultra high molecular weight polyethylene artificial joint component according to claim 16, wherein said block has a thickness, after compression, of at least 5 mm in a direction perpendicular to the compression plane.*

*20. A method for producing an ultra high molecular weight polyethylene artificial joint component according to claim 16, wherein said block, prior to compression, has a thickness of at least 3 cm.*

*21. A method for producing an ultra high molecular weight polyethylene artificial joint component according to claim 18, wherein said cooled block has a melting point of from 135° C. to 155° C.*

*22. A method for producing an ultra high molecular weight polyethylene artificial joint component according to claim 12, wherein said irradiation is conducted in the presence of oxygen.*

*23. A method for producing an ultra high molecular weight polyethylene artificial joint component according to claim 12, wherein said irradiation is conducted under a vacuum or in an inert atmosphere.*

*24. A method for producing an ultra high molecular weight polyethylene artificial joint component according to claim 12, additionally comprising processing said block, after cooling, by a process comprising cutting said block to form said component.*

*25. A method of producing an ultra high molecular weight polyethylene artificial joint component according to claim 12, wherein after said subjecting to pressure step, said block is subjected to isothermal crystallization.*

*26. A method for producing an ultra high molecular weight polyethylene artificial joint component according to claim 12, wherein after said subjecting to pressure step, said block is subjected to isothermal treatment at a temperature of from around 100° C. to 130° C. for a period of from 1 hour to 20 hours.*

*27. A method of making an artificial joint component having improved abrasion resistance, the artificial joint component being obtained by fabrication from a crosslinked ultra high molecular weight polyethylene (UHMWPE) which is prepared by the method comprising:*

*a) providing raw UHMWPE in the form of a rod;*

*b) crosslinking the rod with gamma-irradiation at a dose of at least 1 MR;*

*c) heating the crosslinked rod to a compression deformable temperature below the melting point of the UHMWPE;*

*d) subjecting the heated rod to pressure; and*

*e) cooling and solidifying the rod.*

*28. A method according to claim 27, wherein the dose of gamma-irradiation is 1 MR to 5 MR.*

*29. A method according to claim 27, wherein the compression deformable temperature is greater than the melting point minus 50° C.*

*30. A method according to claim 28, wherein pressure is applied in step d) to deform the rod.*

*31. A method according to claim 30, wherein the deformed rod is cooled in a compression deformed state.*

*32. A method of producing a UHMWPE artificial joint component comprising making a crosslinked UHMWPE according to claim 27 and processing the rod after solidification to form the joint component.*

*33. A method according to claim 32, wherein the joint component is selected from hip, knee, elbow, finger, and shoulder.*

*34. A method according to claim 32, wherein the joint component is a hip component or a knee component.*

* * * * *